(12) United States Patent
Balberg et al.

(10) Patent No.: US 7,515,948 B1
(45) Date of Patent: Apr. 7, 2009

(54) PHOTOACOUSTIC ANALYZER OF REGION OF INTEREST IN A HUMAN BODY

(75) Inventors: Michal Balberg, Jerusalem (IL); Revital Pery Shechter, Rishon Lezion (IL); Michal Olshansky, Tel Aviv (IL)

(73) Assignee: Ornim Inc., Wilmington, DE (US)

( * ) Notice: Subject to any disclaimer, the term of this patent is extended or adjusted under 35 U.S.C. 154(b) by 863 days.

(21) Appl. No.: 10/938,880

(22) Filed: Sep. 13, 2004

Related U.S. Application Data

(60) Provisional application No. 60/502,208, filed on Sep. 12, 2003, provisional application No. 60/502,209, filed on Sep. 12, 2003.

(51) Int. Cl.
*A61B 5/1455* (2006.01)
(52) U.S. Cl. ............... 600/323; 600/338; 600/473; 600/476
(58) Field of Classification Search ......... 600/310, 600/323, 407, 473, 476
See application file for complete search history.

(56) References Cited

U.S. PATENT DOCUMENTS

| | | | | |
|---|---|---|---|---|
| 5,167,231 A | * | 12/1992 | Matsui | ............ 600/459 |
| 5,348,002 A | * | 9/1994 | Caro | ............ 600/310 |
| 5,494,032 A | | 2/1996 | Robinson et al. | |
| 5,555,885 A | | 9/1996 | Chance | |
| 6,041,248 A | | 3/2000 | Wang | |
| 6,498,942 B1 | | 12/2002 | Esenaliev et al. | |
| 6,690,958 B1 | | 2/2004 | Walker et al. | |
| 6,738,653 B1 | | 5/2004 | Sfez et al. | |
| 6,846,288 B2 | * | 1/2005 | Nagar et al. | ............ 600/437 |

OTHER PUBLICATIONS

Keinle et al "In vivo determination of the optical properties of muscle with time-resolved reflectance using a layered model" Physics Medicine Biology 44 (1999) pp. 2689-2702.

Lev A. et al "Direct, noninvasive detection of photon density in turbid media" Optics Letters vol. 27, No. 7, (2002) pp. 473-475.

Lev et al "Ultrasound tagged light imaging in turbid media in a reflectance geometry" Optics Letters vol. 25, No. 6, (Mar. 15, 2000) pp. 378-380.

(Continued)

*Primary Examiner*—Eric F Winakur
*Assistant Examiner*—Etsub D Berhanu
(74) *Attorney, Agent, or Firm*—Browdy and Neimark, PLLC

(57) ABSTRACT

A method and apparatus are presented for non-invasively monitoring at least one characteristic of a region of interest in a body. The body is illuminated by pulsed light to induce a photoacoustic effect. Acoustic radiation is detected, and measured data indicative thereof is generated. The photoacoustic effect is controlled by carrying out at least one of the following: providing the pulsed light of at least two different wavelength, analyzing the measured data to determine time variations of at least one predetermined parameter of a time dependent acoustic signal for each of wavelength, and determining oxygen saturation level in the region of interest; and operating a plurality of acoustic elements configured for detection of the acoustic radiation, to thereby define a focal volume for acoustic radiation detection to match dimensions of the region of interest.

40 Claims, 10 Drawing Sheets

OTHER PUBLICATIONS

Leveque-Fort et al "In situ local tissue characterization and imaging by backscattering acousto-optic imaging" Optics Communication 196 (2001) pp. 127-131.

Oraevsky A.A. et al "Measurement of tissue optical properties by time-resolved detection of laser-induced transient stress" Applied Optics vol. 36, No. 1 (Jan. 1, 1997) pp. 402-415.

F. Rousseau et al "Robust and Automatic Calibraton Method for 3D Freehand Ultrasound" Medical Image Computing and Computer Assisted Intervention, MICCAI'03, Montreal, Canada, (Nov. 2003).

Shen Y et al "Measurement of the optical absorption coefficient of a liquid by use of a time-resolved photoacoustic technique" Applied Optics, vol. 39, No. 22 (Aug. 1, 2000) pp. 4007-4012.

Yao G et al "Theoretical and experimental studies of ultrasound-modulated optical tomography in biological tissue" Applied Optics vol. 39, No. 4 (Feb. 1, 2000) pp. 659-664.

A. Zourabian et al "Trans-abdominal monitoring of fetal artierial blood oxygenation using pulse oxymetry" Journal of Biomedical Optics, vol. 5, No. 4, (Oct. 2000) pp. 391-405.

\* cited by examiner

PHOTOACOUSTIC ANALYZER OF REGION OF INTEREST IN A HUMAN BODY

RELATED APPLICATIONS

The present application claims the benefit of U.S. Provisional Appln. No. 60/502,208, filed Sep. 12, 2003, and U.S. Provisional Appln. No. 60/502,209, filed Sep. 12, 2003, the entirety of which are hereby incorporated by reference in their entirety.

FIELD OF THE INVENTION

This invention relates to medical devices and methods, and more specifically to such devices and methods for non-invasive analysis of a region of interest in a human body.

BACKGROUND OF THE INVENTION

The well being of a mammal (e.g. human) may be assessed and monitored by determining the level of oxygen saturation in the blood or tissue using the method of oximetry or pulse oximetry. Conventional pulse oximetry uses an apparatus that emits light of at least two wavelengths to irradiate a tissue volume and collects light that propagated through a portion of the tissue containing pulsating blood. The collected light at the two wavelengths is analyzed to determine the heart rate of the subject and the degree of oxygen saturation of the tissue or blood being monitored. Oximetry and pulse oximetry can be performed in transmission or reflection geometries. However, it can provide inaccurate readings in the presence of ambient light, in cases of low perfusion of blood and during motion of the subject or the portion of tissue being examined.

The well-being of the fetus inside the uterus is traditionally monitored by measuring the fetal-heart-rate (FHR) by placing sensors on the skin of the mother's abdomen directed at the fetus or the fetal heart. A normal fetal-heart-rate (FHR) pattern is usually associated with the delivery of a normal well-oxygenated infant; however, a non-reassuring FHR is not always associated with the delivery of a compromised infant.

In the case of a non-reassuring FHR, the fetal blood oxygen saturation level can be measured indirectly by either fetal head sampling, which measures the pH level of the fetal blood, or by directly attaching a pulse oximeter to the presenting part of the fetal head during labor. Both of these methods are performed following the rupture of membranes where the fetal head and/or cheeks can be reached.

Assessing the maturity of fetal lungs is one of the major concerns of pre-term deliveries. If the baby is delivered and the lungs are not mature, the baby may develop Respiratory Distress Syndrome (RDS), which can result either in fetal death or in long-lasting periods of repeated respiratory difficulty.

In cases where intervention is considered in the course of pregnancy (such as caesarean section or induction of labor) and there is a need to assess the maturity of the lungs, amniotic fluid is drained. Measuring phospholipids in amniotic fluid as the lecithin/sphingomyelin ratio using thin-layer chromatography has been the established clinical procedure for predicting fetal lung maturity. Although it is the clinical gold standard method, it remains a time-consuming process, has a large intralaboratory and interlaboratory coefficient of variation, and requires expertise. In addition, the procedure of amniotic fluid drainage itself is invasive and suffers a small risk of abortion. Additional techniques that are used for assessing lung maturity levels include measuring the number of lamellar bodies in a volume of amniotic fluid, measuring the prostaglandin level in amniotic fluid and measuring the fluorescence polarization of a sampled amniotic fluid.

When a fetus is acutely distressed, for example as a result of strangulation by the umbilical cord, the bowel content, meconium, may be passed into the amniotic fluid. Assessment of meconial contamination of amniotic fluid is important in the management of late pregnancy. It appears in nearly one third of all fetuses by 42 weeks of gestation. In cases where the fetus gasps during delivery, inhaling the sticky meconium into the upper respiratory tract results in partial airways obstruction. Meconium aspiration syndrome occurs in 0.2% to 1% of all deliveries and has a mortality rate as high as 18%. The disease is responsible for 2% of all prenatal deaths.

To date, meconium stained amniotic fluid is diagnosed following the rupture of membranes, when the amniotic fluid is drained. However, in cases where the fetus head is tightly fitted in the pelvis, the amniotic fluid is not drained, preventing detection of any potentially harmful outcome to the respiratory tract.

Several methods for determining the optical properties of a tissue in a body are known in the art. These include: near infrared spectroscopy (for example using time resolved spectroscopy as disclosed in U.S. Pat. No. 5,555,885), ultrasound tagging of light (for example Yao G et al. Applied Optics Vol. 39 pg 659-664, February 2000) and photoacoustic spectroscopy (for example Oraevsky A. A. et al. Applied Optics Vol. 36 pg 402-405, January 1997). In each of these technologies electromagnetic radiation is used to interact with the tissue, where the interaction depends on the absorption and scattering properties of the components composing the tissue or fluid. Consequently by monitoring this interaction at one or several wavelengths one can extract the optical properties of the tissue and determine the concentration of its components. For imaging a tissue in two or three dimensions the signals are collected and analyzed per pixel or voxel in the target volume. In order to determine the local concentrations of different components tomographic algorithms are used when the light distribution is detected (as in near infrared spectroscopy and ultrasound tagged light) or time dependent signals are analyzed in cases where acoustic energy is detected (as in photoacoustic spectroscopy). The major research and development effort in the above mentioned technologies has been to improve imaging resolution and sensitivity per pixel or voxel.

U.S. Pat. No. 6,498,942 discloses an apparatus for optoacoustic monitoring of blood oxygenation. The apparatus includes a radiation source of pulsed radiation and a probe having a front face to be placed in close proximity to or in contact with a tissue site of an animal body. The probe further includes a plurality of optical fibers terminating at the surface of the front face of the probe and connected at their other end to a pulsed laser. The front face of the probe also has mounted therein or thereon a transducer for detecting an acoustic response from blood in the tissue site to the radiation pulses connected to a processing unit which converts the transducer signal into a measure of venous blood oxygenation

SUMMARY OF THE INVENTION

The present invention provides an optimized analyzer for analyzing the presence and/or concentration of a substance in a region of interest of a body. The region of interest may include tissues and/or liquid substances. It should be understood that the term "tissues analyzer" used herein refers to the analyzer of liquid-containing region of interest as well.

The tissue analyzer of the invention includes an illumination unit, an acoustic unit, and a control unit. The illumination unit is configured to illuminate body tissues with light pulses having at least one wavelength. As light pulses propagate through the body tissues, they are absorbed by chromophores in the tissues. Absorption of light generates acoustic signals via a photoacoustic effect. The acoustic unit is configured for receiving acoustic signals and generating measured data indicative thereof. The acoustic unit comprises a single acoustic element or a plurality of acoustic elements. The acoustic element is an acoustic receiver, or optionally— acoustic transceiver. The acoustic unit generates signals (measured data) in response to and indicative of acoustic signals generated in the illuminated tissue region. A processor, being a part of the control unit, is configured to analyze signals generated by the acoustic unit.

According to one aspect of the invention the processor determines time variations of at least one predetermined parameter of the time dependent acoustic signal for each of at least two wavelengths. The processor then uses these time dependent variation to determine oxygen saturation level in the region of interest.

Alternatively or additionally, the control unit is configured and operable to define a focal volume for collection of sound waves (acoustic radiation) to match dimensions of the region of interest, such that the acoustic unit collects a substantial portion of these sound waves during a predetermined time window $\Delta t$. It should be understood that such a matching region may be the entire region of interest or a portion thereof. This technique improves the signal to noise ratio (SNR) of the detection system, enabling use of safer light energies for illumination. The collected signals are processed and analyzed to determine the presence, and optionally, the amount or concentration, of a substance in the region of interest in the irradiated body tissues or fluids.

In one embodiment, the above matching is achieved by configuring the processor to activate the acoustic elements according to a predetermined temporo-spatial pattern so as to define the desired focal volume. The signals generated by the acoustic elements are temporally integrated by the acoustic unit or by the processor according to a temporo-spatial pattern, for example, using methods and apparatuses used in ultrasound phased arrays or linear arrays, such as (but not limiting): delay-line integration, dynamic depth focusing and convolution of detected sound waves. For example, all of the acoustic elements may be activated continuously and the processor configured to receive a separate signal from each acoustic element having a predetermined temporal delay, and to integrate the signals into a single signal. In another embodiment, the appropriate operation of the acoustic elements consists of activating all the elements and processing the measured data so as to extract the acoustic radiation collected from the desired focal volume, by sampling signals generated by the acoustic elements according to the predetermined temporo-spatial pattern.

The tissue analyzer of the invention may be used in analyzing parameters of a fluid in a fluid reservoir (e.g. amniotic fluid). In this application, the concentration of a structure or a component within the amniotic fluid, such as lamellar bodies, meconium and blood are determined by monitoring the optical properties of a portion of the fluid, such as the absorption coefficient, the reduced scattering coefficient and the refractive index of the fluid. Wavelength selection is based on the absorption and scattering coefficients of the amniotic fluid in the presence of lamellar bodies, meconium or blood. The invention may also be used for noninvasive measurement of the optical properties of other extravascular body fluids such as pleural, pericardial, peritoneal and synovial fluids.

The device of the invention may be used, for example in oximetry or pulse oximetry, in fetal oximetry or pulse oximetry.

In pulse oximetry, temporal changes in a blood volume due to the cardiac cycle are determined by monitoring the time dependent (low-frequency (0.5-2.5 Hz)) changes in the high frequency (1 kHz-100 MHz) time dependent acoustic signal generated by absorption of light pulses at the two wavelengths, by oxygenated and deoxygenated hemoglobin. The processor operates to extract from the measured data a data portion (subsignals) indicative of the acoustic radiation generated in the region of interest, and then determines slow time variations in parameters of the subsignals. These subsignals are generated by the acoustic unit for each wavelength of illumination. The parameters include for example, the amplitude of the signal, or the transient slope of the subsignal, corresponding to changes in the blood volume during the cardiac cycle. These parameters are used to determine the oxygen saturation level of the tissue or blood volume in which acoustic waves, corresponding to the subsignals, are generated.

Thus, according to one broad aspect of the invention, there is provided a device for non-invasive analysis in a region of interest of a body medium, the device comprising:

(a) an illuminator configured to produce pulsed light of at least two different wavelengths;

(b) an acoustic unit configured and operable to collect acoustic radiation and generate data indicative thereof, the acoustic unit being operable to collect acoustical radiation at a location on a body surface generated in the region of interest by a photoacoustic effect when the region of interest is irradiated with the illuminating pulsed light and generate measured data indicative of the received radiation; and (c) a processor configured to receive the measured data, and analyze the received data to determine at least one desired characteristic of the region of interest, the processor being preprogrammed to carry out at least one of the following:

i) determining time variations of at least one predetermined parameter of a time dependent acoustic signal in the collected acoustic radiation for each of said at least two wavelengths, and determining oxygen saturation level in the region of interest;

ii) operating a plurality of acoustic elements of the acoustic unit to thereby define a focal volume for the acoustic radiation collection, said focal volume matching dimensions of the region of interest.

According to another broad aspect of the invention, there is provided a device for non-invasive analysis of a region of interest in a body medium, the device comprising:

(a) an illumination unit producing pulsed light;

(b) an acoustic unit configured to collect acoustic radiation and generate measured data indicative thereof, the acoustic unit comprising a plurality of independent acoustic elements, each acoustic element producing a measured signal in response to and indicative of collected acoustic radiation at a location on a body surface generated in the body medium by a photoacoustic effect when the acoustic unit is applied to the body surface and the body medium is irradiated with the illuminating light; and (c) a processor configured to operate the acoustic unit to thereby define a focal volume for the acoustic radiation collection to match dimensions of the region of interest.

According to yet another broad aspect of the invention, there is provided a device for non-invasive pulse oximetry in a region of interest of a body, the device comprising:
  (a) an illumination unit configured and operable to produce pulsed light of at least two different wavelengths;
  (b) an acoustic unit configured to generate data indicative of received acoustic radiation, the acoustic unit being operable to receive acoustical radiation at a location on a body surface generated in the region of interest by a photoacoustic effect when the region of interest is irradiated with the illuminating pulsed light and generate measured data indicative of the received radiation; and
  (c) a processor configured to receive and analyze the measured data, to determine time variations of at least one predetermined parameter of the time dependent acoustic signal for each of said at least two wavelengths, and determine oxygen saturation level in the region of interest.

According to yet another broad aspect of the invention, there is provided a method for non-invasive analysis of a region of interest of a body, the method comprising:
  controlling photoacoustic measurements in a medium including the region of interest, while irradiating the region of interest with pulsed light, to induce the photoacoustic, effect detecting acoustic radiation coming from the medium as a result of the photoacoustic effect, generating measured data indicative thereof; and analyzing the measured data to monitor the region of interest; said controlling comprising at least one of the following:
  i) providing said pulsed light of at least two different wavelength, determining in said measured data time variations of at least one predetermined parameter of a time dependent acoustic signal for each of said at least two wavelengths, and determining oxygen saturation level in the region of interest;
  ii) operating a plurality of acoustic elements configured for said detection of the acoustic radiation, to thereby define a focal volume for acoustic radiation detection to match dimensions of the region of interest.

According to yet another aspect of the invention, there is provided a method for non-invasive oximetry in a region of interest of a body, the method comprising:
  illuminating the region of interest with pulse light of at least two different wavelengths detecting acoustic radiation coming from the medium as a result of a photoacoustic effect, and generating measured data indicative thereof; and
  processing and analyzing the measured data to monitor at least one characteristic of the region of interest, said processing and analyzing comprising determining time variations of at least one predetermined parameter of a time dependent acoustic signal for each of said at least two wavelengths, and determining oxygen saturation level in the region of interest.

According to yet another aspect of the invention, there is provided a method for non-invasive analysis of a region of interest of a body, the method comprising:
  illuminating the region of interest with pulsed light to induce a photoacoustic effect;
  controlling operation of a plurality of acoustic elements to define a focal volume for detection of acoustic radiation to match dimensions of the region of interest;
  processing and analyzing measured data indicative of the detected acoustic associated with the region of interest to monitor at least one characteristic of the region of interest.

BRIEF DESCRIPTION OF THE DRAWINGS

Non-limiting examples of embodiments of the present invention are described below with reference to figures attached hereto, which are listed following this paragraph. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF THE INVENTION

Figure 1:
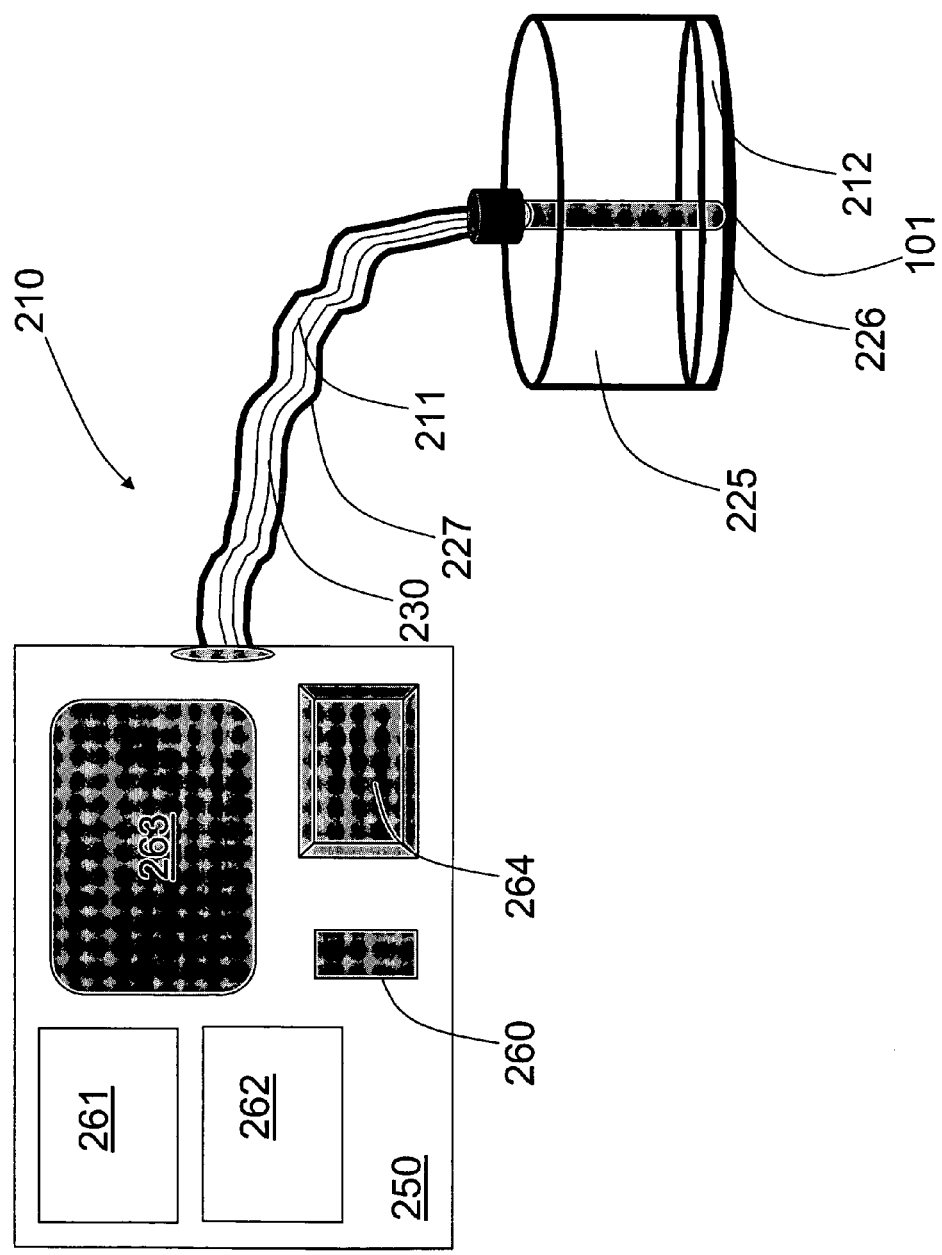
FIG. 1 shows schematically a tissue analyzer in accordance with one embodiment of the invention.

FIG. 1 shows a schematic diagram of a tissue analyzer 210 of the present invention. The tissue analyzer 210 includes an illumination unit 260 (e.g., a pulsed laser); a processor 261 having a memory 262, a data presentation utility (display) 263 and an input/output control panel 264; and an acoustic unit 212. In the present example, the illumination unit and processor form parts of a common controller 250. A hand held (or fixed) probe head 225 has a probe surface 226 that is adapted for application onto a body surface. The probe head 225 is connected to the controller 250 by light guiding means (optical fiber 211, for example, located in a flexible sheath 227. The optical fiber 211 conducts light energy from the illumination unit 260 to a distal end 101 of the optical fiber 211 located at probe surface 226 in order to irradiate body tissues adjacent to the probe surface 226 when the probe surface is applied to a body surface. The acoustic unit 212 is located in the probe head 225 and detects sound waves generated in body tissues and arriving at the probe surface 226 when the probe surface is applied to a body surface. The acoustic unit 212 is connected to the controller 250 via a communication line that may be wired and/or a wireless communication system. For example, the acoustic unit 212 may be connected to the controller 250 via a cable 230 inside the sheath 227 extending from the acoustic unit 212 to the controller 250. Illumination unit 260 may optionally be placed inside probe head 225, such that its output port 101 is in contact with a body surface.

Figure 2:
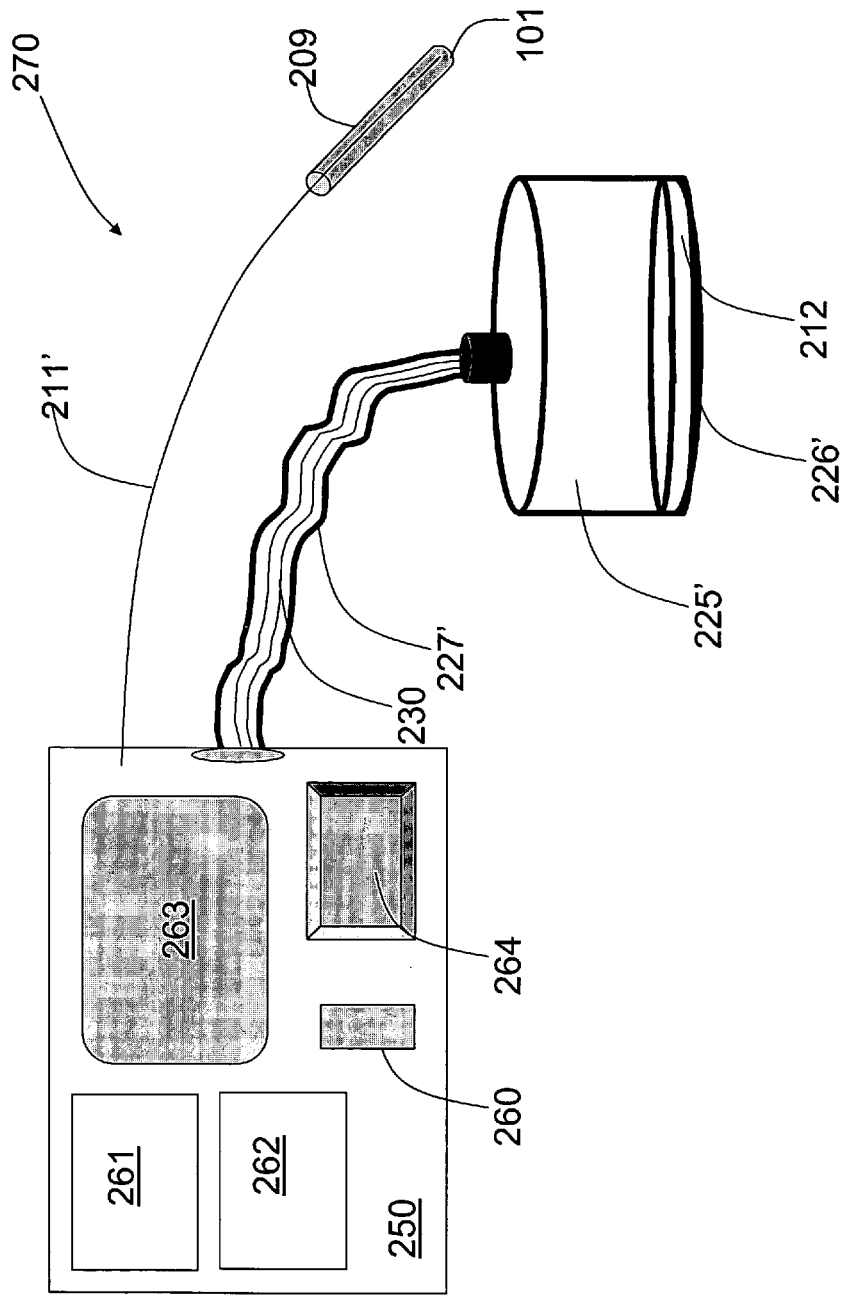
FIG. 2 shows a tissue analyzer in accordance with another embodiment of the invention.

FIG. 2 shows a tissue analyzer 270 in accordance with another embodiment of the invention. Elements in the tissue analyzer 270 in common with the tissue analyzer 210 of FIG. 1 are indicated by the same reference numerals, without further comment. In the tissue analyzer 270, an optical fiber 211' conducts light from the illumination unit 260 to a probe 209 located at the distal end 101 of the optical fiber 211'. The probe 209 is configured to be placed in a different location on a body surface than probe head 225' (for example probe 209 is inserted into a tract, such as vagina or esophagus) for irradiating body tissues from the different location with light conducted by the optical fiber 211' from the illumination unit 260 to the probe 209. A probe head 225' has a probe surface 226' that is acoustically adapted for application onto a body surface. An acoustic unit 212 is located in the probe head 225 that detects sound waves generated in body tissues and arriving at the probe surface 226 when the probe surface is applied to a body surface. The acoustic unit 212 is connected to the controller 250 via a communication line that may be a wired or a wireless communication system. For example, the acoustic unit 212 may be connected to the controller 250 via a cable 230 inside a sheath 227' extending from the acoustic unit 212 to the controller 250. In this embodiment, the optical fiber 211' is not enclosed in the sheath 227'.

Generally, the acoustic unit may include one or more acoustic elements configured and operable to collect acoustic radiation and generate measured data indicative thereof. The acoustic unit receives acoustical radiation at a location on a body surface generated in the region of interest by a photoacoustic effect when the region of interest is irradiated with the illuminating pulsed light and generates measured data indicative of the received radiation. According to one operational mode of the invention, the apparatus (including one or more acoustic elements) is configured and operable to determine time variations of at least one predetermined parameter of the time dependent acoustic signal for each wavelength of the illuminating light, and determine oxygen saturation level in the region of interest.

Figure 3A:
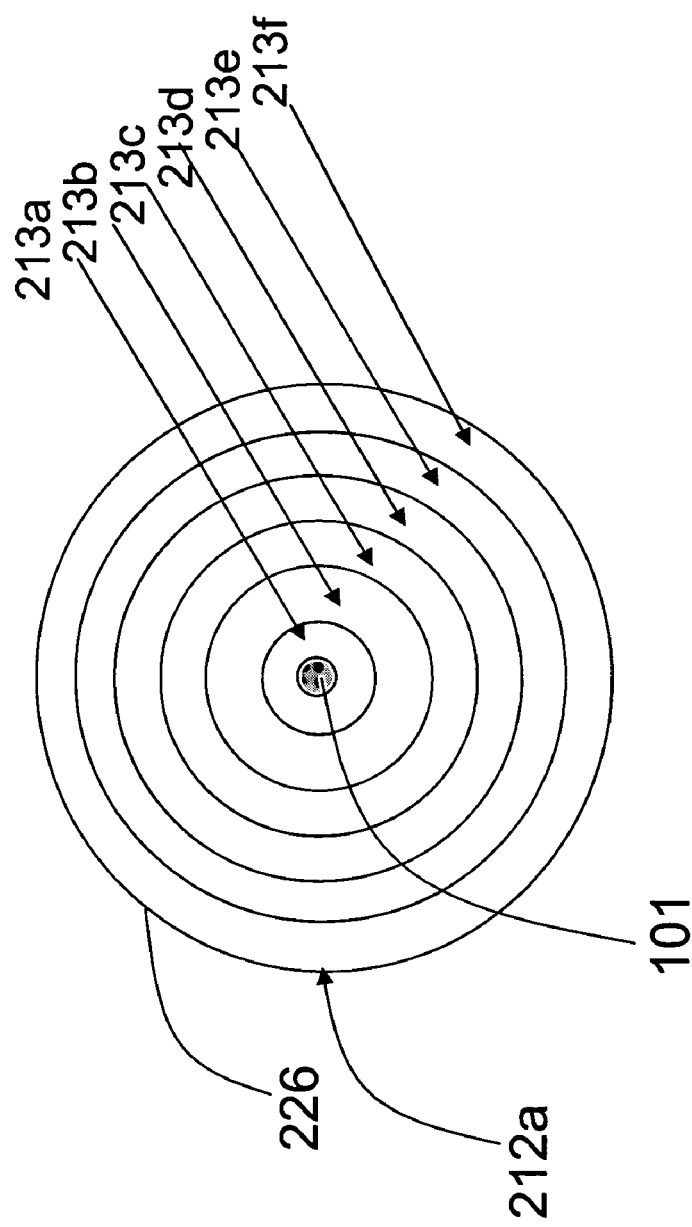
FIGS. 3A and 3B show two examples, respectively, of an arrangement of a plurality of acoustic elements of the acoustic unit.
Figure 3B:
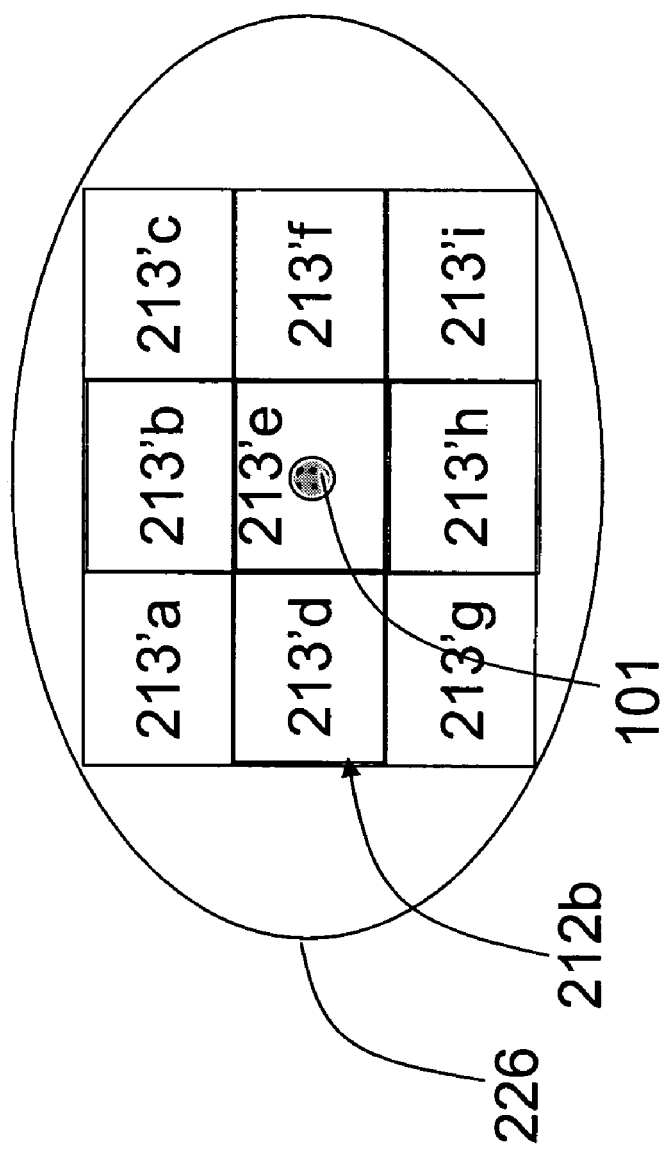

In accordance with another configuration and operation of the invention, the acoustic unit includes a plurality of independent acoustic elements. FIGS. 3A and 3B show two examples of the acoustic unit 212.

In the example of FIG. 3A, an acoustic unit 212a is shown having a plurality of acoustic elements arranged in concentric arrays—six concentric annular acoustic elements 213a-213f being shown in the figure. This is by way of example only, it being possible to carry out the invention using any number of acoustic elements, generally at least two such elements. The annular acoustic elements 213 surround the distal end 101 of the optical fiber 211. In the example of FIG. 3b, an acoustic unit 212b is shown having a plurality of acoustic elements arranged in a two dimensional array—nine rectangular acoustic elements 213'a to 213'i being shown in the figure. This is by way of example only, it being possible to carry out the invention with any number of such acoustic elements, generally at least two elements. The array of acoustic elements 213' surrounds the distal end 101 of the optical fiber 211. It is clear that for the tissue analyzer 270, where the distal end 101 of optical fiber 211' is placed outside the probe head 225, a similar arrangement of acoustic elements can be used.

As an example, each element 213 and 213' is defined by a pair of electrodes, one at the bottom surface and one at the top surface of a piezoelectric material (such as Polyvinylidene Fluoride (PVDF), or lead zirconate titanate (PZT)). Each element is independently activatable by applying a voltage signal to a pair of electrodes corresponding to that element. As acoustic waves impinge on surface 226 of acoustic units 212a or 212b, and the activated acoustic elements receive these signals and generate electric signals indicative thereof. The processor 261 is configured and operable to define a focal volume for the acoustic radiation collection to match dimensions of the region of interest. This may be achieved by activating only some of the acoustic elements, and/or collect the received signals from some of the acoustic elements.

Figure 4:
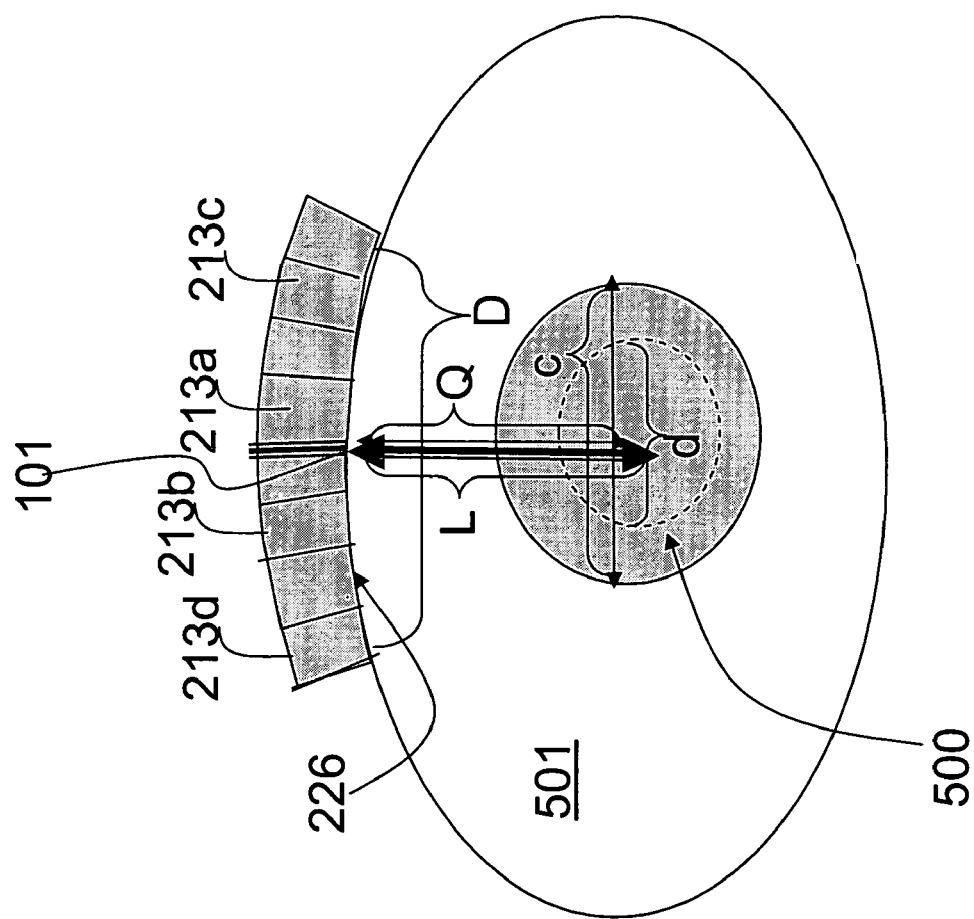
FIG. 4 exemplifies a focal volume defined by the acoustic unit configuration of FIG. 3A to match a region of interest.

Thus, according to one example, the processor 261 determines the activation of acoustic elements according to a predetermined temporo-spatial pattern. FIG. 4 exemplifies an acoustic unit utilizing the acoustic elements arrangement of FIG. 3A, showing a side view of a probe head 225 (only a subset of acoustic elements 213 being shown in the figure) Probe surface 226 is placed in acoustic and optic contact with the skin of a subject 501, overlaying a region of interest 500. Distal end 101 of optical fiber is placed at the center of the acoustic unit. The region of interest is preferably an ellipsoid having a center at a distance Q from the center of the probe surface 226, and has a shortest cross sectional axis of dimension c in a direction parallel to the face of acoustic unit 212. The desired focal volume (to be defined by operating the acoustic elements, e.g., by activation of the acoustic elements) is determined by a focal length L and a cross sectional dimension d that optimally match the dimensions Q and c respectively. (The figure is exaggerated for clarity). Matching is determined by the processor 261 by optimization algorithms such as minimal difference or maximum likelihood, such that the focal volume of the acoustic elements (i.e., activated acoustic elements or those from which the signals are collected) is equal to or smaller than the region of interest.

Turning back to FIG. 1, according to an embodiment of the present invention, the processor 261 controls the operation of the tissue analyzer 210. To this end, the processor 261 is configured to receive the values of various geometrical measures relating to the body under examination and store them in the memory 262. Such geometrical measures include, for example, the dimensions of various body tissues and body cavities. These geometrical measures may be obtained, for example, using a conventional ultrasound imaging system to image body tissues and body cavities in the subject and analyzing the image or images to determine the required parameters or the optimal positioning of probe head 225 on the body surface. It should be noted that the acoustic unit 212 used for measurements can optionally be a part of such an imaging system. The geometrical measures determined prior to the actual measurements and forming the so-called "reference data" may be input to the processor using the data input port 264.

Based on the geometrical measures and/or images so-determined, the processor 261 determines the region of interest, using for example image processing algorithms such as edge detection. Alternatively or additionally, the operator defines the region of interest on the image using the input data port 264. Turning to FIG. 4, the region of interest is defined by its lateral distance Q from the probe surface 226 and by its cross-sectional size c (in two dimensions). Then, the processor 261 defines a focal volume of the acoustic unit, having a focal length L and a cross section of diameter d to match the determined dimensions of the region of interest.

The processor 261 then determines the acoustic elements of the acoustic unit 212 that are to be activated, or in the case all the elements are activated—determines those acoustic elements from which the acoustic signals are to be sampled, for optimally transducing acoustic signals generated in the region of interest into electric signals as explained below.

The processor 261 controls the activation of the illumination unit 260 to emit light pulses through the skin into the region of interest and analyzes the electric signals generated in the determined acoustic elements in response to acoustic waves generated in the region of interest via a photoacoustic effect according to any given application (such as the two examples given below), to determine presence or concentrations of desired substances in the region of interest.

Thus, the processor is configured to receive signals generated by the acoustic unit 212 and to analyze the signals so as to collect acoustical data from a focal volume located within a region of interest in a body region. In one embodiment, the processor is configured to activate the acoustic elements according to a predetermined temporo-spatial pattern so as to collect acoustical data from the focal volume. The signals generated by the acoustic elements are temporally integrated (by the acoustic unit or by the processor) so that a single signal indicative of the acoustic radiation collected within the desired focal volume presents the measured data to be processed and analyzed. For example, in the array of concentric annular acoustic elements 213 shown in FIG. 3A, the acoustic elements 213 may be activated sequentially starting with the acoustic element 213a nearest to the center of the array, so that the acoustic element 213a is activated and subsequently deactivated, then the element 213b is activated and subsequently deactivated, and so on until a sufficient number of acoustic elements have been activated to collect acoustical data from a focal volume at a focal length L, having a predetermined cross sectional dimension d. The rate of the activation and deactivation steps is determined according to the speed of the acoustic waves in the body tissue or tissues, so as to collect acoustical data from a focal volume inside the body, as is known in the art. This temporo-spatial pattern of activation is repeated until the collection of acoustical data from the focal volume is completed. The array of rectangular acoustic elements shown in FIG. 3b may be operated similarly, so that the time period that each one of acoustic elements 213' is sampled is proportional to its distance from the center of the array. The signals generated by the acoustic elements are temporally integrated by the acoustic unit 212 or the processor and the integrated signal is analyzed as described below.

As indicated above, in another embodiment, all of the acoustic elements are activated continuously and the processor is configured to receive a separate signal from each acoustic element. The processor is further configured to sample each of the plurality of signals input from the acoustic elements at predetermined times so as to collect acoustical data from the focal volume. For example, in the array of concentric annular acoustic elements 213 shown in FIG. 3A, the signals may be sampled sequentially starting from the signal from the acoustic element 213a nearest to the center of the array, so that the signal from the acoustic element 213 is sampled, then the signal from the element 213b is sampled, and so on until signals have been sampled a sufficient number of acoustic elements so as to collect acoustical data from a focal volume having predetermined dimensions L and d, as is known in the art. This temporo-spatial pattern of signal sampling is repeated until the collection of acoustical data from the focal volume is completed. Signals from the array of rectangular acoustic elements shown in FIG. 3B may be sampled similarly so that the time that each one of acoustic elements 213' is sampled is proportional to its distance from the center of the array.

In yet another embodiment, all of the acoustic elements are activated continuously and the processor is configured to receive a separate signal from each acoustic element. The processor is further configured to sample each of the plurality of signals input from the acoustic elements so as to collect acoustic data from the focal volume. For example, in the array of concentric annular acoustic elements 213 shown in FIG. 3A, the signals may be sampled sequentially starting from the signal from the acoustic element 213 furthest to the center of the array, so that the signal from the acoustic element 213f is sampled, then the signal from the element 213e is sampled, and so on until signals have been sampled a sufficient number of acoustic elements so as to collect acoustical data from a focal volume having a predetermined lateral dimension, as is known in the art. This temporo-spatial pattern of signal sampling is repeated until the collection of acoustical data from the focal volume is completed. Signals from the array of rectangular acoustic elements shown in FIG. 3b may be sampled similarly so that the time that each one of acoustic elements 213' is sampled is proportional to its distance from the center of the array.

Alternatively or additionally, other temporo-spatial processing and/or activation of the acoustic elements to collect data from a focal volume (e.g., using a phased array of acoustic elements such as delay-line integration or convolution) may also be used. In such embodiments acoustic unit 212 may comprise a conventional ultrasound imaging system configured to collect from a focal volume.

The temporo-spatial pattern of acoustic element activation or signal sampling, allows the acoustic unit 212 to function as a phased array of acoustic elements so as to collect acoustical data from a focal volume below the skin surface. The focal volume is characterized by its depth L below the skin surface and its cross-sectional dimension d. For a circular aperture of the transducer (such as the one shown in FIG. 3A), the diameter D of the activated acoustic element array is determined by the ratio L/d according to the formula $$D=2.44\lambda_s L/d, \quad [1a]$$

where $\lambda_s$ is a characteristic wavelength of generated acoustic waves in the body tissue. As the acoustic wavelengths may span a broad-band range, processor 261 optionally determines a characteristic wavelength $\lambda_s$, or varies the collection dimension D as to account for collecting different acoustic wavelengths.

Whereas for a rectangular aperture (as shown in FIG. 3B) the ratio L/d is determined by the width D of the activated or sampled portion of the acoustic element array according to the formula $$D=2\lambda_s L/d \quad [1b]$$

Similar relations can be used by processor to determine a value for D in other geometrical configurations (such as a single element acoustic unit or a linear array). Alternatively, acoustic unit 212 may comprise an array of focused acoustic elements, each having a different focal volume, and processor 261 operates the ensemble of focused acoustic elements to collect acoustic signals generated in the predetermined focal volume.

Figure 5:
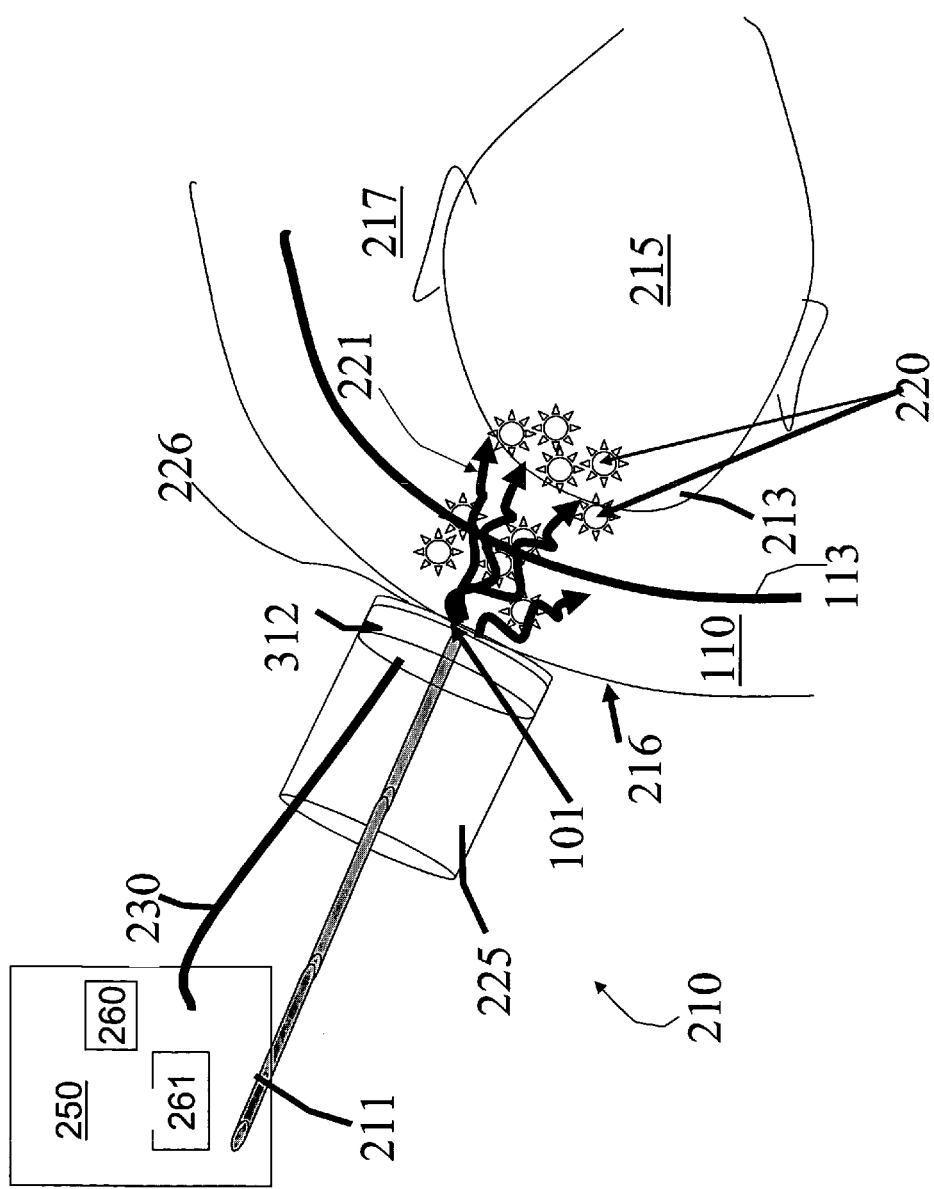
FIG. 5 exemplifies the tissue analyzer of FIG. 1 operable for measuring fetal blood oxygen saturation.

FIG. 5 shows the tissue analyzer 210 configured as shown in FIG. 1 for use in determining oxygen saturation levels in blood (also known as "oximetry" or 'pulse oximetry') of an intrauterine fetus. The probe head 225 is applied to maternal skin 216 overlaying a uterus and amniotic sac 217 of a gravida. The probe surface 226 is coupled to the maternal skin 216 via an acoustic coupling agent such as a gel or an adhesive patch that couples both acoustic and optic waves between the skin and probe surface with minimal attenuation.

In this application, the region of interest is the fetal head (other organs or tissues of the fetus may be chosen). The probe head 225 is positioned on the maternal skin 216 preferably at a location at which it is at a minimum distance from the fetal head, as determined from an image, such as an ultrasound image.

Probe head 225 includes acoustic unit 312 and distal end 101 of optical fiber 211. It should be noted that according to this embodiment, acoustic unit 312 may include a single acoustic element, or a plurality of acoustic elements.

In this application, the processor 261 is configured to operate the illumination unit 260 so as to generate light pulses with at least two wavelengths, for example, $\lambda_1$ and $\lambda_2$. One wavelength is in the range of 605-805 nm and the other wavelength is in the range of 800-1300 nm. The processor 261 is preferably configured to operate the illumination unit 260 so as to generate intermittent trains of pulses of alternative wavelengths with a different time gating or a time delay sufficiently short so that the optical characteristics of the tissue region or fluid essentially do not change between consecutive pulses of different wavelengths. For example, a time delay of less than 10 msec between successive pulses may be used, when monitoring changes in blood volume associated with the cardiac cycle. The pulses may have duration of 10-1000 nsec. The light pulses are conducted by the optical fiber 211 to the probe surface 226. At the probe surface 226, light pulses 221 propagate through the maternal skin 216 into maternal tissues 110 and the amniotic sac 217 until they arrive at fetal head 215. As light pulses 221 propagate through maternal and fetal tissues they are absorbed by chromophores in the tissues. Absorption of light generates acoustic waves 220 (marked as starbursts) via a photoacoustic effect. The acoustic waves 220 propagate through the fetal and maternal tissues, and a portion of these acoustic waves 220 arrives at the acoustic unit 312. Due to the nature of the light energy 221 delivered to the skin surface 216, the acoustic waves arrive at the acoustic unit 312 as time varying pressure signals (generally, the time dependent acoustic signals), where each signal is the result of a pulsed optical energy of a particular wavelength ($\lambda_1$ or $\lambda_2$). The acoustic unit 312 detects the pressure signals and generates one or more voltage signals (measured data) in response to and indicative of each acoustic signal propagating through the maternal skin 216, as explained above.

The processor 261 is configured to analyze the time dependent signals generated by acoustic unit 312 so as to determine an oxygen saturation level (S) of maternal and/or fetal blood, as explained below. The saturation S is defined as the ratio between the concentration of oxygenated hemoglobin [HbO] and the total concentration of hemoglobin [HbT] in the blood:

$$S=[HbO]/[HbT], \quad [2]$$

where [HbT]=[HbO]+[Hb] and [Hb] is the concentration of deoxygenated hemoglobin.

Figure 6:
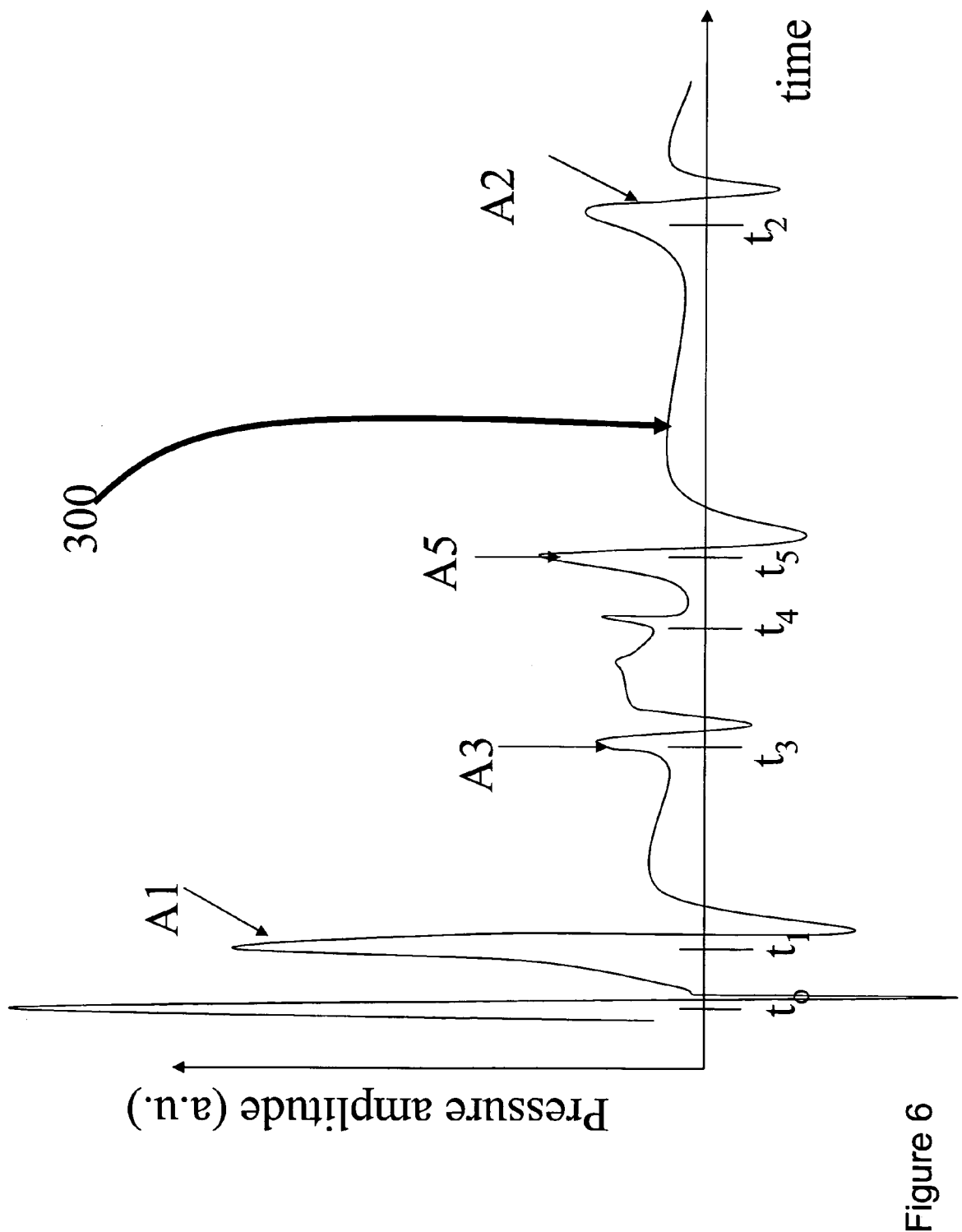
FIG. 6 shows an exemplary signal generated by the acoustic unit of the tissue analyzer of the invention for measuring fetal oxygen saturation.

FIG. 6 shows an exemplary time dependent signal 300 collected following the initiation of one pulse of light radiation of one wavelength. The processor 261 is configured to cause the illumination unit 260 to deliver, for each wavelength $\lambda$ ($\lambda_1$ or $\lambda_2$), a train of pulses over at least one fetal heart beat so as to obtain a collection sequences of signals of the type shown in FIG. 6 over at least one fetal heart beat, and stores them in memory. For each signal, the processor 261 is configured to identify the subsignal A2, namely a data portion indicative of the acoustic radiation generated in the region of interest. The subsignal A2 in the signal 300 (i.e. the portion of the signal corresponding to sound waves generated at the fetal head) is identified by the processor 261 as the amplitude of the acoustic signal starting at the time $t_2$ that corresponds to the distance Q between the surface 213 of fetal head 215 and the probe surface 226 (FIG. 5), obtained, for example, from an ultrasound image previously stored in the memory 262. Time $t_2$ may, for example, be determined from an A-mode scan of the ultrasound beam, when acoustic pulses from fetal head reach surface 226. It should be noted that the processor 261 may start the collection of acoustic signals only at time $t_2$ after the illumination was initiated, to thereby collect the acoustic radiation substantially from the region of interest, and ignore other signals. Parameters of subsignal A2 (i.e. the amplitude of the peak or the time dependent slope) at the two wavelengths used for illumination are determined, and the oxygen saturation level is determined based on the principles of either oximetry or pulse oximetry.

In an application of the present invention, the processor 261 is configured to analyze the signals so as to carry out oximetry or pulse oximetry. In this case, processor 261 stores detected signals in the memory 262 for each emitted light pulse at each wavelength. At every time step of predetermined duration $\Delta\tau$ the stored signals are analyzed to determine the parameters of subsignal A2 (i.e. the amplitude of the peak and/or the time dependent slope) and stores in memory the determined parameters as a function of time to determine an oxygen saturation level. In other words, the processor operates to determine the time variations of at least one predetermined parameter of the time dependent acoustic signal for each of the at least two wavelengths.

In applications involving oximetry, $\Delta\tau$ can be large (ranging from 0.1 to 100 seconds), whereas in applications involving pulse oximetry $\Delta\tau$ is shorter than the duration of half of the cardiac cycle of the subject being monitored (preferably $\Delta\tau<100$ msec): In applications involving pulse oximetry, the processor 261 is further configured to analyze the sequence of signals during each time $\Delta\tau$ and determine the determined parameters (or a time average of the determined parameters). Processor 261 then uses the time dependent sequence of determined parameters at consecutive durations of length $\Delta\tau$, to determine maximum and minimum values (or the time averaged maximum and minimum values) of the determined parameter (or parameters) of subsignal A2 over at least one heart cycle. For each wavelength $\lambda$ ($\lambda_1$ or $\lambda_2$), processor 261 determines the difference $\Delta OD^\lambda$ between the maximum and the minimum values of the determined parameter (or parameters) over a fetal cardiac cycle. In cases where $\Delta OD^\lambda$ corresponds to the optical density at each wavelength, the relation between $\Delta OD^\lambda$ and the saturation S is:

$$S = \frac{\mu_{Hb}^{\lambda 1} - R\mu_{Hb}^{\lambda 2}}{R(\mu_{HbO}^{\lambda 2} - \mu_{Hb}^{\lambda 2}) + (\mu_{Hb}^{\lambda 1} - \mu_{HbO}^{\lambda 1})} \quad [3]$$

where $$R = \frac{\Delta OD^{\lambda 1}}{\Delta OD^{\lambda 2}}$$

and $\mu_{HbO}^\lambda$, $\mu_{Hb}^\lambda$ are the molar attenuation coefficients of oxygenated and deoxygenated hemoglobin, respectively, at wavelength $\lambda$ ($\lambda=\lambda 1, \lambda 2$). The values of $\mu_{HbO}^\lambda$, $\mu_{Hb}^\lambda$ are known from the literature.

The processor 261 is configured to calculate S using Eq. 3 from the determined $\Delta OD^\lambda$, and the input values of the $\mu_{HbO}^\lambda$, $\mu_{Hb}^\lambda$. Other, similar equations can be used, by adapting equation 3 to correspond to the determined parameters using relations known in the art for photoacoustic analysis of tissue properties.

The processor 261 may also determine the pulse rate of the fetus by using methods and algorithms of pulse oximetry, where the data to be processed are the time dependent variation of the determined parameter (or parameters) of subsignal A2. For example, the time difference between maximal (or minimal) values of the determined parameter at each wavelength corresponds to the reciprocal of the pulse rate. Other techniques of low frequency analysis of the data (such as Fourier transforms) can also be used.

As explained above, the processor 261 identifies the signal A2 from the time $t_2$ it arrives at the probe surface 226. Since the fetus may move during the measurement (i.e. the distance Q between the fetal head and the probe surface may change), the time $t_2$ at which the signal A2 reaches the acoustic unit 212 may change. The processor may be configured to determine the corresponding time $t_2$. For example, statistically known shifts in time $t_2$ due to normal fetal movements may be used as allowed time windows around the original $t_2$. Other methods such as time binning or correlations may also be used for determining reasonable shifts in fetal position. Alternatively, a new image of the fetus may be obtained and the value of Q (FIG. 5) in the image determined and updated in the memory 262 of the processor 261 and/or the probe head moved to a new optimal position on the maternal skin. During uterine muscle contractions the time difference $\Delta$ (whereas $\Delta=(t_5-t_1)$) between signals A1 and A5 changes, and this change may be used to monitor contractions and the strength of contractions.

The invention may also be used to determine temporal changes in the maternal blood volume due to the maternal cardiac cycle or more generally to determine the oxygen saturation level of a human or an animal, by pulse oximetry. In this application, the low-frequency changes (0.5-2.5 Hz) in subsignal A3, starting at $t_3$, corresponding to maternal tissues, are monitored as described above for the determination of temporal changes in the fetal blood volume. Thus, both the maternal oxygen saturation and pulse rate may be determined.

According to an aspect of the present invention, acoustic unit 312 comprises a plurality of acoustic elements configured to collect acoustic signals from a focal volume matched to the region of interest identified as the fetal head, as explained above for acoustic unit 212. The diameter D of the activated or sampled acoustic elements is determined using Equations 1a or 1b above, so as to operate the acoustic unit as a phased array defining a focal volume contained within this region of interest. The processor 261 is operated so as to collect acoustic data from this focal volume and process the integrated signal as to determine oxygen saturation by pulse oximetry as explained above for acoustic unit 312. As explained above, the time $t_2$ associated with acoustic signals from the region of interest may shift, thus value of L and d (FIG. 5) used by the processor in Equation 1a or 1b should be updated, and the corresponding diameter D be re-determined.

The processor 261 displays the determined fetal and/or maternal oxygen saturation level and heart rate as a function of time on the display 263. The processor 261 may optionally issue an alert (by emitting a sound or light signal) when the oxygen saturation level drops below a predetermined threshold (for example, an oxygen saturation level 30% or 40%) or when the fetal heart rate changes abnormally.

Figure 7:
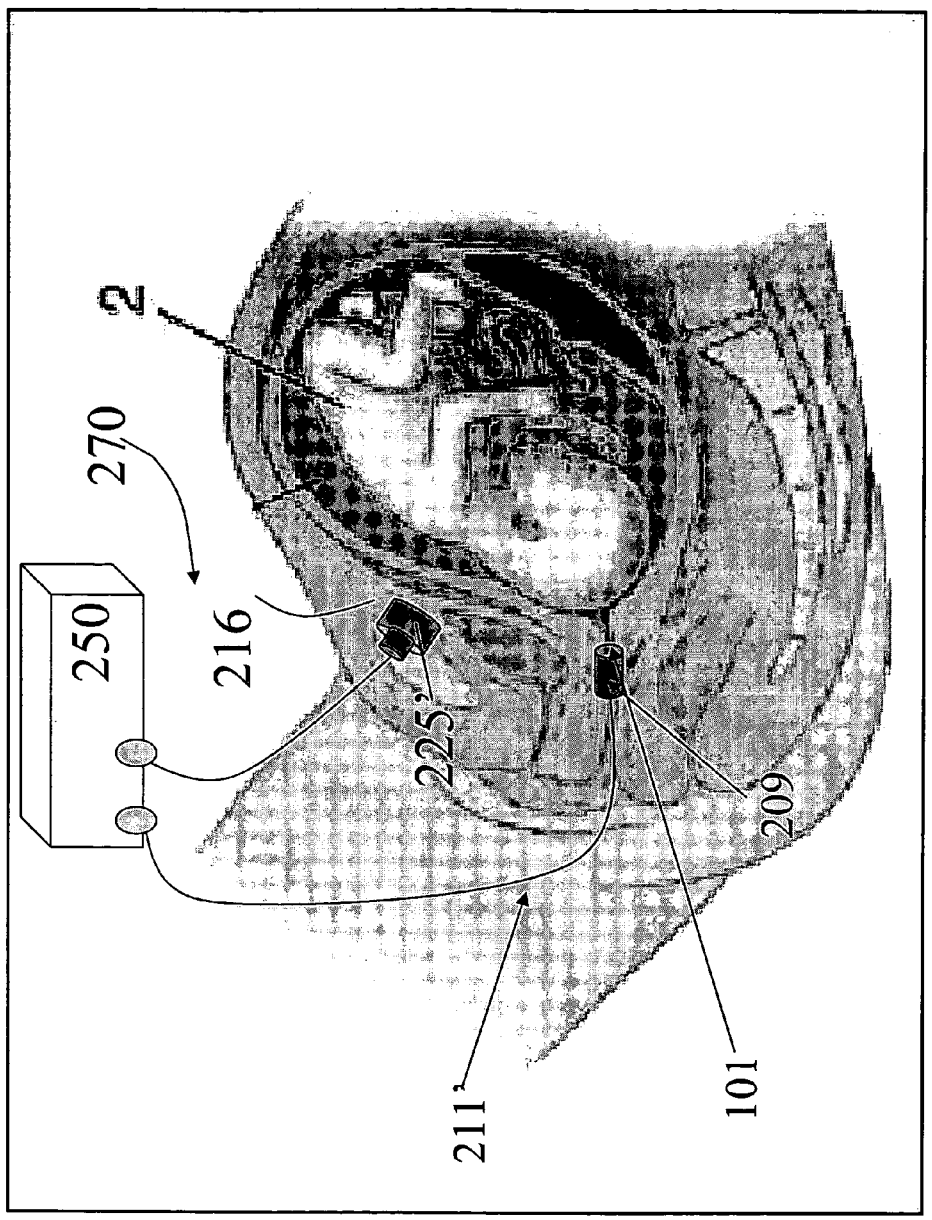
FIG. 7 exemplifies the tissue analyzer of FIG. 2 operable for measuring fetal blood oxygen saturation.

FIG. 7 shows a tissue analyzer 270 configured as shown in FIG. 2 for use in oximetry or pulse oximetry. A probe 209 containing the distal end 101 of an optical fiber 211' is positioned in the vaginal tract adjacent to the cervix. A probe head 225' is positioned on a maternal skin 216. The tissue analyzer 270 is then used as described above for the operation of the tissue analyzer 210.

According to an embodiment of the present invention, when more than one fetus is present inside the uterus, the oxygen saturation level of each fetus is measured independently using the same apparatus, or several different apparatuses are used—one for each fetus. Each fetus is located using an ultrasound imaging system, and the optimal arrangement of illumination units and acoustic element(s) is determined for monitoring the oxygen saturation level of each fetus.

Figure 8:
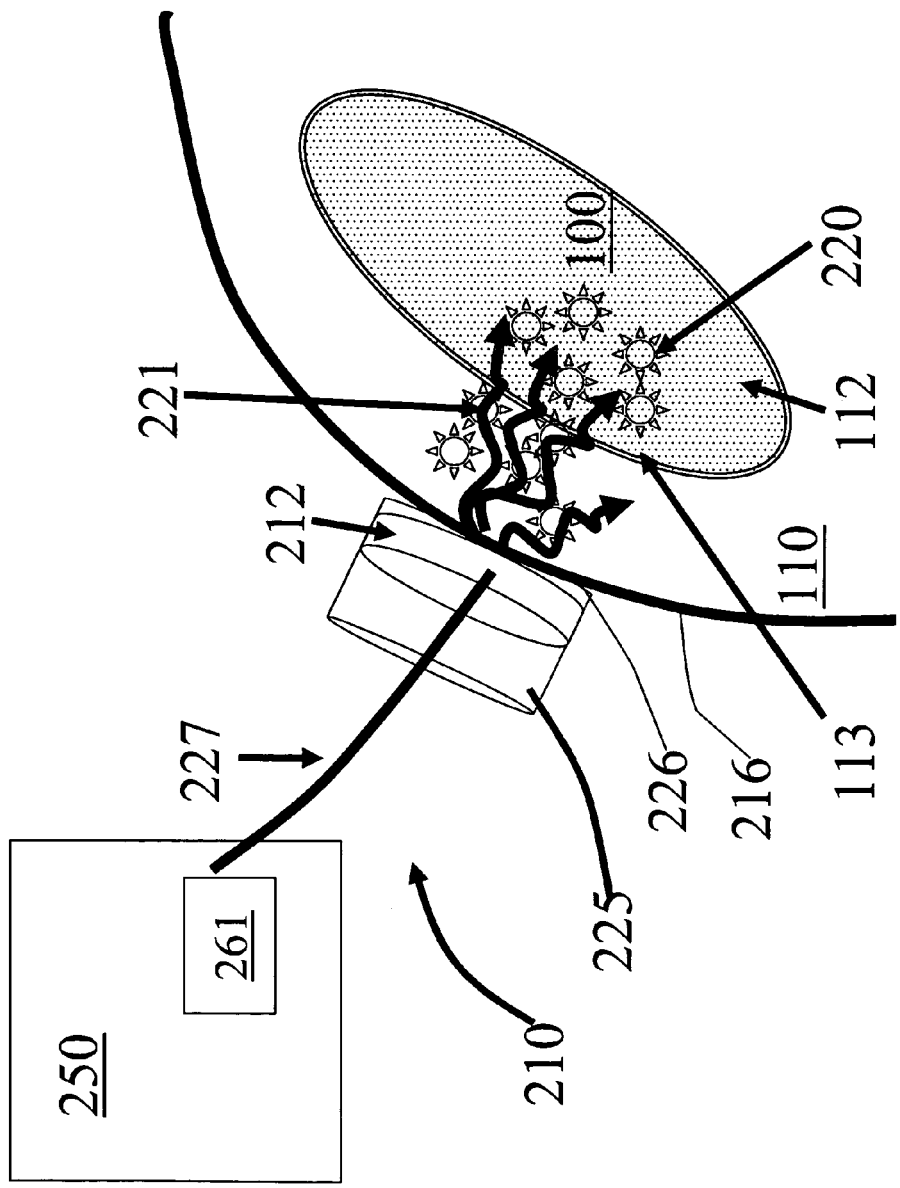
FIG. 8 exemplifies the tissue analyzer of FIG. 1 operable for analyzing amniotic fluid.

FIG. 8 shows a tissue analyzer 210 configured as shown in FIG. 1 for use in analyzing amniotic fluid 112 in an amniotic sac 100. In this application, the region of interest is the amniotic fluid 112. A probe head 225 is therefore applied to maternal skin 216 overlaying a uterus and amniotic sac 100 of a gravida and the tissue analyzer 210 is operated so as to collect acoustic data from a focal volume contained within this region of interest. The probe surface 226 is coupled to the maternal skin 216 via an acoustic coupling agent (not shown) such as a gel or an adhesive patch that couples both acoustic and optic waves between the skin and probe surface with minimal attenuation. In this application, a processor 261 is configured to receive as an input the distance L of a volume of amniotic fluid from the probe surface 226, and the cross sectional dimension d of the focal region. The processor 261 then determines the diameter D of the acoustic elements to be sampled and/or activated using, for example, Equations 1a or 1b above The concentration of a structure or a component within the focal volume of fluid 112, such as lamellar bodies, meconium and blood, can be determined in accordance with the invention, for example, by measuring the optical properties of a portion of the fluid. These optical properties may include for example the absorption coefficient, the reduced scattering coefficient and the refractive index of the fluid. Methods to determine optical properties of a fluid from a time dependent acoustic signal generated by the photoacoustic effect are known in the art, for example as disclosed in Shen Y. et al. Applied Optics, Vol 39, issue 22, page 4007-4012, August 2000. The calculated concentration may optionally be compared to a threshold level as described below.

The acoustic unit 212 collects a substantial portion of pressure waves generated in the amniotic fluid 112. For example, the temporal duration $\Delta t$ of the pressure wave generated within an amniotic fluid volume of 1 $cm^3$ is of the order of 0.3-1 msec. In order to detect high-resolution temporal variations within this time period, wide band acoustic elements are preferably used. Alternatively, a subarray of acoustic elements (for each element 213 in acoustic unit 212a or 213' in acoustic unit 212b) each optimized to collect acoustic signals at a predetermined frequency bandwidth can be used.

In this application, body tissues and fluids are irradiated by a plurality of wavelengths (produced by the illumination unit 260) that are highly scattered by the lamellar bodies contained in amniotic fluid in order to determine the reduced scattering coefficient of the fluid. The plurality of wavelengths is preferably less absorbed by water. Such wavelengths may be chosen, for example, in the range of visible to near infrared light, from 600 nm-1300 nm.

Lamellar bodies are produced by type II alveolar cells in increasing quantities as fetal lungs mature. They are composed almost entirely of phospholipids and represent the storage form of pulmonary surfactant. Their diameter is about 0.5-2 μm, and their index of refraction is about 1.475. Consequently, when using the above range of wavelengths, Mie scattering dominates the scattering of light from lamellar bodies. The choice of specific wavelengths depends on the SNR of the apparatus used. The difference in wavelengths used for illumination has to provide a sufficient change in the scattering coefficient that can be detected by the system. The relationship between the wavelength $\lambda$ and the reduced scattering coefficient $\mu_{s'}$ of monodisperse scattering dielectric spheres is known in the literature to be.

$$\mu_{s'} = 3.28\pi a^2 \rho \left(\frac{2\pi a}{\lambda}\right)^{0.37} (m-1)^{2.09} \quad [4]$$

where $a$ is the average radius of the dielectric spheres, $\rho$ is their volume density, $\lambda$ is the optical wavelength in vacuum, and $$m = \frac{n_s}{n_0}$$

where $n_s$ and $n_0$ are the refractive index of the spheres and the surrounding material respectively.

Light pulses at a plurality of wavelengths are generated by the illumination unit 260. Wavelength selection is based on the absorption and scattering coefficients of the amniotic fluid in the presence of lamellar bodies or meconium. For example, amniotic fluid without blood or meconium, absorbs light at wavelengths 700-900 nm almost equally. Therefore, light distribution in the focal volume contained within the amniotic fluid depends primarily on the scattering characteristics of the fluid, i.e. on the reduced scattering coefficient, and therefore on the wavelength of light used for illumination. The time dependent photoacoustic pressure wave generated in the amniotic fluid depends on the light distribution within the fluid and consequently on the scattering coefficient. Processor 261 activates illumination units emitting pulses at different wavelengths (for example 735 nm and 780 nm being equally absorbed in water) and stores in memory the time dependent pressure profiles at each wavelength respectively. Processor 261 then uses these profiles to determine a measure corresponding to the reduced scattering coefficient of the media verus wavelength (for example the slope of the temporal decay of the signals within the focal volume). It then uses equation 4, or a modified equation 4 (that depends on physiological parameters of amniotic fluid and not on monidisperse spheres) to determine the concentration $\rho$ of the lamellar bodies.

As another example, it is known that meconium primarily contains blood and bilirubin. The absorption coefficient depends on the product of the concentration of meconium or blood within the fluid and the molar absorption coefficients (which are known in the art). In order to determine the absorption coefficient, following the determination of the reduced scattering coefficient at the above wavelengths (735 nm and 785 nm), different wavelengths which are differently absorbed in the fluid (such as 1064 nm or 600 nm) are used for illumination and time dependent pressure signals are obtained. From the rate of decay of the signal at each wavelength, the optical attenuation is obtained. In the case where the diffusion approximation is satisfied, the optical attenuation $\mu_{eff}$ is known to depend on both the reduced scattering coefficient $\mu_{s'}$, and the absorption coefficient $\mu_a$, where $\mu_{eff} = \sqrt{3\mu_a(\mu_a + \mu_{s'})}$ since the reduced scattering coefficients were determined as above, the absorption coefficients at each wavelength is extracted.

Figure 9:
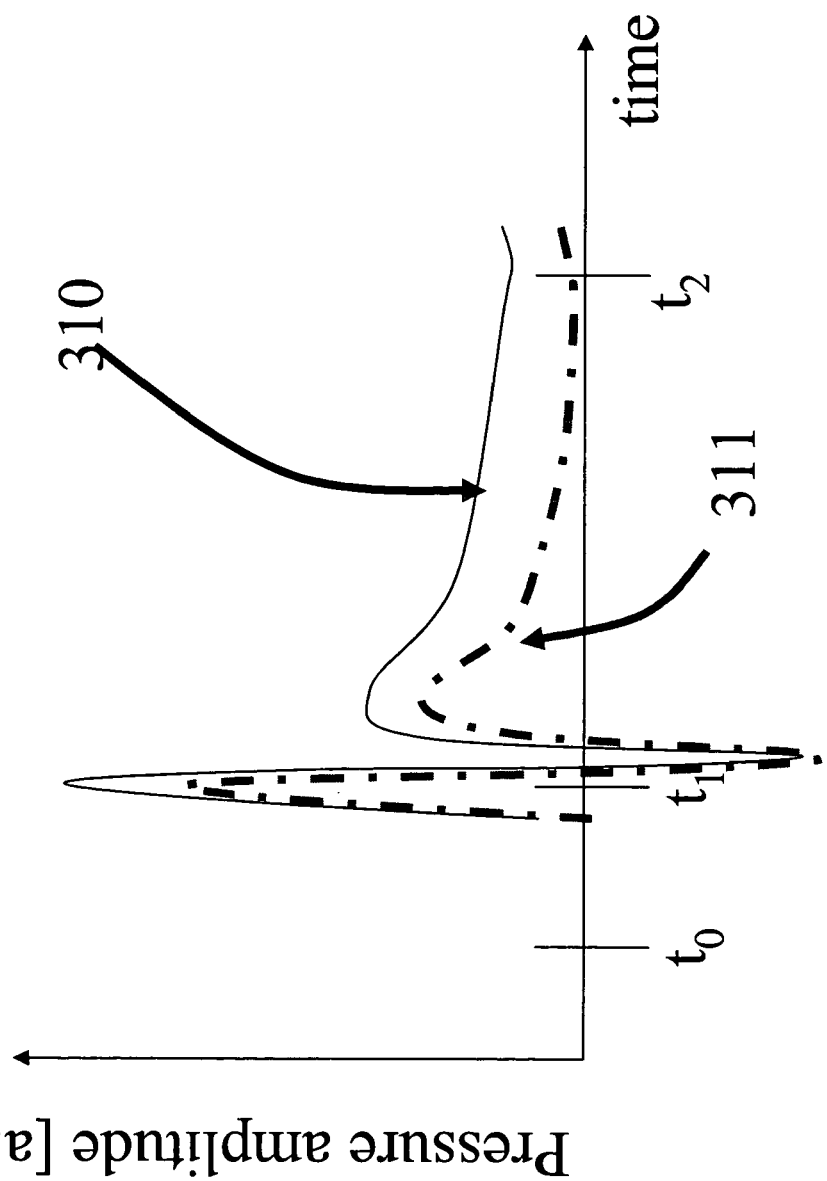
FIG. 9 shows an exemplary signal generated by the acoustic unit of the tissue analyzer of the invention for analyzing amniotic fluid.

An exemplary signal generated by the acoustic unit 212 is schematically shown in FIG. 9. Graphs 310 and 311 show the time dependent pressure amplitude generated in maternal tissues and amniotic fluid following the onset of an optical pulse 221 at time $t_0$. For clarity, the signal generated between times $t_0$ and $t_1$ are not shown in FIG. 9. At time $t_1$, a pressure signal is generated at the interface 113 between outer membrane of amniotic sac and amniotic fluid and between time $t_1$ and $t_2$ pressure waves are generated within amniotic fluid 112. The signals 310 and 311 were generated using different exemplary wavelengths (for example 735 nm and 780 nm) The signals 310 and 311 have different amplitudes and time dependency due to the different attenuation at the different wavelengths in the various tissues and fluids, as well as the different scattering of each wavelength in the amniotic fluid. Different parameters of the signal (such as the pressure amplitude at time $t_1$ or the temporal decay of the pressure amplitude between time $t_1$ and $t_2$) are used by the processor 261 to determine reduced scattering coefficient $\mu_{s'}$ and consequently the concentration of different components in the fluid as explained above.

A threshold value for mature lungs may be stored in the memory 262. In some embodiments of the present invention, several parameters are stored in the memory 262. Some parameters are obtained by analysis of ultrasound images, such as, the thickness of the uterine wall or the thickness of abdominal wall. Additional parameters may include the weight of gravida and the duration of the gestation (relative to last menstrual period or based on other indicators). Some of these parameters are used to calculate the threshold value to which the optical properties of the fluid, or the concentration of lamellar bodies are to be compared. These parameters can optionally be used to calculate the concentration of the lamellar bodies from the acoustic signals according to a specific algorithm which includes all layers in the tissue 110 surrounding the amniotic sac 100.

The tissue analyzer 270 of FIG. 2 may also be used in analyzing amniotic fluid similar to the way the tissue analyzer 210 is used. As shown in FIG. 7, probe unit 209, including the distal end 101 of optical fiber 211', is inserted transvaginally to illuminate the amniotic fluid through the cervix. The probe head 225' is positioned on the maternal skin 216. The tissue analyzer 270 is then used as described above for the tissue analyzer 210. However, the wavelengths used for transcervical illumination may be different than the wavelengths used for abdominal illumination, since the composition of the illuminated tissue layers is different in both cases. For example skin (epidermis) contains melanin that highly absorbs in the ultraviolet region, whereas the cervix has little or no melanin.

While it is preferred that the concentration of lamellar bodies or meconium be calculated by the processor from the recorded signals, it is not always necessary to actually calculate these concentrations from the recorded signals. A database of signals can be stored in the memory 262 or features of such signals (e.g. amplitude, phase, frequency, time dependence, wavelets or principal components). The database may contain data from measurements obtained for premature fetal lungs and mature fetal lungs. For lung maturity classification by the database, a similarity metric is defined. Obtained signals are classified according to the best fit to mature or immature lungs using clustering, neural networks and/or other classification algorithms. For meconium analyses, the database can contain signals from stained and clear amniotic fluid. Features from the ultrasound image taken prior or during the assay are used to categorize the measured signals in the database.

The processor 261 displays the determined concentration of lamellar bodies, meconium or blood, and optionally displays a "mature" or "premature" indication on the display 263, without quantitative information about the concentration of lamellar bodies, or a display of "stained" or "clear" for the case of meconium staining.

The tissue analyzer of the invention can be operated in an imaging mode where the illumination units and acoustic unit are scanned over a region of interest and signals responsive to light scattered by tissues are collected to determine averaged optical properties of tissue regions. These optical properties are input to the processor 261.

Whereas the above examples relate to measuring the optical properties of amniotic fluid, similar apparatuses can be designed for noninvasively measuring the optical properties of other extravascular fluids such as pleural (around the lungs), pericardial (around the heart), peritoneal (around the abdominal and pelvis cavities) and synovial (around the joints) fluids.

The invention claimed is:

1. A device for non-invasive analysis in a region of interest of a body medium, the device comprising:
    (a) an illuminator configured to produce pulsed light of at least two different wavelengths;
    (b) an acoustic unit configured and operable to collect acoustic radiation and generate data indicative thereof, the acoustic unit being operable to collect acoustical radiation at a location on a body surface generated in the region of interest by a photoacoustic effect when the region of interest is irradiated with the illuminating pulsed light and generate measured data indicative of the received radiation; and
    (c) a processor configured to receive the measured data, and analyze the received data to determine at least one desired characteristic of the region of interest, said at least one desired parameter comprising a cross-sectional dimension of the region of interest, the processor being preprogrammed to carry out at least one of the following:
        i) determining time variations of at least one predetermined parameter of a time dependent acoustic signal in the collected acoustic radiation for each of said at least two wavelengths, and determining oxygen saturation level in the region of interest;
        ii) operating a plurality of acoustic elements of the acoustic unit to thereby define a focal volume for the acoustic radiation collection, said focal volume matching dimensions of the region of interest.

2. The device according to claim 1(ii), wherein the processor is configured to selectively activate the acoustic elements according to a predetermined temporo-spatial pattern.

3. The device according to claim 2, wherein the processor is configured to process the measured data by sampling signals generated by the acoustic elements according to the predetermined temporo-spatial pattern.

4. The device according to claim 1 (ii), wherein the processor is configured to process the measured data by sampling signals generated by the acoustic elements according to a predetermined temporo-spatial pattern.

5. The device of claim 4, wherein the processor is operable to collect signals from the acoustic elements operating desired dimensions of the focal volume defined by a distance between a center of the region of interest and the acoustic unit and a cross-sectional dimension of the region of interest.

6. The device according to claim 5, wherein the processor is operable to process signals generated by the plurality of the acoustic elements to collect the signals associated with a circular region having a diameter D satisfying $D=2.44\lambda_s L/d$, where $\lambda_s$ is a characteristic wavelength of the acoustic radiation in the region of interest, L defines a distance between the center of the region of interest and the acoustic unit; and d defines the cross-sectional dimension of the region of interest.

7. The device according to claim 5, wherein the processor is operable to process signals generated by the plurality of the acoustic elements to collect the signals associated with a rectangular region having a small width D satisfying $D=2\lambda_s L/d$, where $\lambda_s$ is a characteristic wavelength of the acoustic radiation in the region of interest, L defines the distance between the center of the region of interest and the acoustic unit, and d defines the cross-sectional dimension of the region of interest.

8. The device of claim 1, wherein the acoustic unit comprises a phased array of the acoustic elements.

9. The device of claim 1(ii), wherein the acoustic elements are configured as a phased array.

10. The device of claim 1(i), wherein the acoustic unit comprises at least one acoustic element.

11. The device of claim 1(ii), wherein the processor is operable to selectively activate the acoustic elements such that the activated acoustic elements operate desired dimensions of the focal volume defined by a distance between a center of the region of interest and the acoustic unit and a cross-sectional dimension of the region of interest.

12. The device according to claim 11, wherein the processor is operable to selectively activate the acoustic elements such that the activated acoustic elements form a circular region having a diameter D satisfying $D=2.44\lambda_s L/d$, where $\lambda_s$ is a characteristic wavelength of the acoustic radiation in the region of interest, L defines a distance between the center of the region of interest and the acoustic unit; and d defines the cross-sectional dimension of the region of interest.

13. The device according to claim 11, wherein the processor is operable to selectively activate the acoustic elements such that the activated acoustic elements form a rectangular region having a small width D satisfying $D=2\lambda_s L/d$, where $\lambda_s$ is a characteristic wavelength of the acoustic radiation in the region of interest, L defines a distance between the center of the region of interest and the acoustic unit, and d defines the cross-sectional dimension of the region of interest.

14. The device according to claim 1(ii), wherein the plurality of the acoustic elements are arranged in concentric arrays.

15. The device according to claim 1(ii), wherein the plurality of the acoustic elements are arranged in a two-dimensional array.

16. The device according to claim 1, wherein the processor is configured to extract, from the measured data, a data portion indicative of the acoustic radiation generated in the region of interest.

17. The device according to claim 1, wherein the processor is configured to operate the acoustic unit at a certain time after the illumination was initiated to thereby collect the acoustic radiation substantially from the region of interest.

18. The device according to claim 1, wherein the illuminator is configured and operable to produce the pulses of the different wavelengths at different times.

19. The device according to claim 1(i), wherein the processor is configured to extract, from the measured data, a data portion indicative of the acoustic radiation produced in the region of interest, and determine the time variations of at least one of amplitude and transient slope parameters of the time dependent acoustic signal produced in the region of interest.

20. The device according to claim 19, wherein the processor is configured to determine a difference between maximal and minimal values of said at least one parameter over a cardiac cycle.

21. The device according to claim 20, wherein the processor is configured to determine oxygen saturation level in the region of interest.

22. The device according to claim 1, configured for the non-invasive analysis of a fetus condition.

23. The device according to claim 1, configured for the non-invasive analysis of at least one of the oxygen saturation level in the region of interest, and an amniotic fluid composition.

24. The device according to claim 1, configured for the non-invasive analysis of a fetal blood oxygen saturation.

25. The device according to claim 1, configured for the non-invasive analysis of a maternal oxygen saturation level of a gravida.

26. The device according to claim 1, configured for the non-invasive analysis of an oxygen saturation level of a mammal.

27. The device of claim 1, where the two different wavelengths are selected as those differently absorbable by oxygenated and deoxygenated hemoglobin in the body.

28. The device according to claim 27, wherein the first wavelength is in a range of about 605-805 nm and the second wavelength is in a range of about 800-1300 nm.

29. The device of claim 1, where the two different wavelengths are selected as those characterized by the same absorption by tissue or fluid components in the body.

30. The device of claim 29, where the two different wavelengths are selected to be differently scattered by tissue or fluid components in the body.

31. The device according to claim 1, configured as an oximeter or pulse oximeter.

32. The device according to claim 1, configured for determining a relative location of the region of interest relative to the acoustic unit.

33. The device according to claim 1, configured for determining a distance between the center of the region of interest and the acoustic unit.

34. The device according to claim 1, comprising an imaging system for imaging the region of interest.

35. The device according to claim 1, comprising an acoustic imaging system for imaging the region of interest.

36. The device according to claim 35, wherein said acoustic imaging system includes said acoustic unit for detecting the photoacoustic effect.

37. A device for non-invasive analysis of a region of interest in a body medium, the device comprising:
 (a) an illumination unit producing pulsed light;
 (b) an acoustic unit configured to collect acoustic radiation and generate measured data indicative thereof, the acoustic unit comprising a plurality of independent acoustic elements, each acoustic element producing a measured signal in response to and indicative of collected acoustic radiation at a location on a body surface generated in the body medium by a photoacoustic effect when the acoustic unit is applied to the body surface and the body medium is irradiated with the illuminating light; and
 (c) a processor configured to operate the acoustic unit to thereby define a focal volume for the acoustic radiation collection to match dimensions of the region of interest and to determine a cross-sectional dimension of the region of interest.

38. The device according to claim 37, wherein the processor is configured for the operation of the acoustic unit by selectively actuating the acoustic elements to define the focal volume matching the region of interest.

39. The device according to claim 37 wherein the processor is configured for the operation of the acoustic unit by processing the measured data produced by the plurality of the acoustic element to define the focal volume matching the region of interest.

40. A device for non-invasive pulse oximetry in a region of interest of a body, the device comprising:
 (a) an illumination unit configured and operable to produce pulsed light of at least two different wavelengths;
 (b) an acoustic unit configured to generate data indicative of received acoustic radiation, the acoustic unit being operable to receive acoustical radiation at a location on a body surface generated in the region of interest by a photoacoustic effect when the region of interest is irradiated with the illuminating pulsed light and generate measured data indicative of the received radiation; and
 (c) a processor configured to receive and analyze the measured data, to determine time variations of at least one predetermined parameter of the time dependent acoustic signal for each of said at least two wavelengths, and determine a cross-sectional dimension of the region of interest and determine oxygen saturation level in the region of interest.

\* \* \* \* \*